United States Patent [19]  
Tamaru et al.

[11] Patent Number: 4,841,005  
[45] Date of Patent: Jun. 20, 1989

[54] TRICYCLODECANE DERIVATIVE

[75] Inventors: Sinji Tamaru; Motonobu Kubo, both of Osaka, Japan

[73] Assignee: Daikin Industries, Ltd., Osaka, Japan

[21] Appl. No.: 155,608

[22] Filed: Feb. 12, 1988

[30] Foreign Application Priority Data

Feb. 12, 1987 [JP] Japan .................................. 62-30255

[51] Int. Cl.$^4$ ...................... C08F 18/20; C08F 120/22
[52] U.S. Cl. ..................... 526/245; 526/282; 560/219; 560/220; 568/817
[58] Field of Search ........................ 526/282, 817, 245; 560/219, 220

[56] References Cited

U.S. PATENT DOCUMENTS 2,454,743 11/1948 Mowry et al. .................. 526/282
3,598,745 8/1971 Dunkel .......................... 568/817

Primary Examiner—C. Warren Ivy
Assistant Examiner—Alex H. Walker
Attorney, Agent, or Firm—Birch, Stewart, Kolasch & Birch

[57] ABSTRACT

A tricyclodecane derivative represented by formula (I):

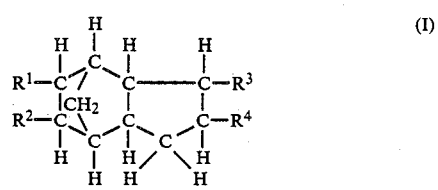

wherein
$R^1$ represents a group $X^1O-$ or a hydrogen atom;
$R^2$ represents a hydrogen atom when $R^1$ represents a group $X^1O-$, or $R^2$ represents a group $X^1O-$ when $R^1$ represents a hydrogen atom;
wherein $X^1$ represents a group

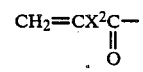

or a hydrogen atom, wherein $X^2$ represents a hydrogen atom, a methyl group, or a trifluoromethyl group;
$R^3$ represents a fluoroalkyl group containing from 1 to 21 carbon atoms, an iodine atom, or a hydrogen atom; and
$R^4$ represents an iodine atom or a hydrogen atom when $R^3$ represents a fluoroalkyl group containing from 1 to 21 carbon atoms, or $R^4$ represents a fluoroalkyl group containing from 1 to 21 carbon atoms when $R^3$ represents an iodine atom or a hydrogen atom.

9 Claims, No Drawings

TRICYCLODECANE DERIVATIVE

FIELD OF THE INVENTION

The present invention relates to a novel acrylate containing a fluoroalkyltricyclodecanyl group, as well as intermediates produced during the synthesis of this novel compound.

BACKGROUND OF THE INVENTION

It has been know that polymers having a tricyclo[5.2.1.0$^{2,6}$]decanyl acrylate or methacrylate as a monomeric component are useful as painting materials and optical materials (as described, for instance in Japanese Patent Application (OPI) Nos. 168009/84, 124605/85, 156708/85 and 166351/85) (the term "OPI" as used herein means an unexamined published Japanese patent application). However, such polymers are defective in that their resistance to water and fouling is insufficient to provide satisfactory paint coatings and that they are too hygroscopic to provide optical materials.

In order to reduce the hygroscopicity of these materials, it is proposed to introduce one or more bromine atoms into the decanyl group (as described in Japanese Patent Application (OPI) No. 124605/85). However, such materials are still insufficient in hygroscopicity. Moreover, the materials have a high refractive index.

SUMMARY OF THE INVENTION

An object of the present invention is to provide a novel acrylate compound containing a fluoroalkyltricyclodecanyl group, as well as intermediates produced during the synthesis of this novel compound.

Another object of the present invention is to provide a painting material which has improved resistance to water and fouling.

A further object of the present invention is to provide an optical material having low hygroscopicity.

A still further object of the present invention is to provide an intermediate capable of reacting with other substances so as to synthesize various compounds.

Other objects of the present invention will be apparent from the following description.

The present inventors conducted intensive studies in order to improve the properties of acrylate polymers containing a tricyclodecanyl group. As a result, the present inventors have found that better results can be attained by introducing a fluoroalkyl group into a cyclodecanyl group. The present invention has been accomplished on the basis of this finding.

The novel tricyclodecane derivative provided by the present invention is a tricyclodecane derivative represented by formula (I):

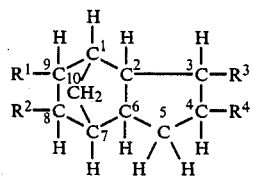

wherein
$R^1$ represents a group $X^1O-$ or a hydrogen atom;
$R^2$ represents a hydrogen atom when $R^1$ represents a group $X^1O-$, or $R^2$ represents a group $X^1O-$ when $R^1$ represents a hydrogen atom;

wherein $X^1$ represents a group

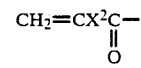

or a hydrogen atom, wherein $X^2$ represents a hydrogen atom, a methyl group, or a trifluoromethyl group;
$R^3$ represents a fluoroalkyl group containing from 1 to 21 carbon atoms, an iodine atom, or a hydrogen atom; and
$R^4$ represents an iodine atom or a hydrogen atom when $R^3$ represents a fluoroalkyl group containing from 1 to 21 carbon atoms, or $R^4$ represents a fluoroalkyl group containing from 1 to 21 carbon atoms when $R^3$ represents an iodine atom or a hydrogen atom.

In formula (I), the numbers on the carbon atoms of the tricyclodecane ring indicate the position numbers of the carbon atoms.

DETAILED DESCRIPTION OF THE INVENTION

The fluoroalkyl group having from 1 to 21 carbon atoms represented by $R^3$ or $R^4$ preferably contains fluorine atoms in an amount of the same number or more as the number of the carbon atoms contained in the group, more preferably in amount of 2 times or more the number of the carbon atoms contained in the group. A perfluoroalkyl group is most preferred. The greater the number of the fluorine atoms present in the fluoroalkyl group, the greater the resistance to water and fouling which is attained by a polymer containing the compound of the present invention.

The number of the carbon atoms present in the fluoroalkyl group is not limited, but in view of the ease of production of the end compound (monomer), those having from 2 to 10 carbon atoms are preferred. Examples of the fluoroalkyl groups having from 2 to 10 carbon atoms include $CF_3CF_2-$, $CF_3(CF_2)_3-$, $CF_3(CF_2)_5-$, $CF_3(CF_2)_7-$, $(CF_3)_2CF-$, $CF_3(CF_2)_3CF(CF_3)-$, and $CF_3(CF_2)_5(CF_2)_2-$.

The trycyclodecane derivative of the present invention can be produced by the following steps:

(1) reacting to a known compound, 8- or 9-hydroxytricyclo[5.2.1.0$^{2,6}$]deca-3-ene (as a starting material) with a fluoroalkyl iodide having from 1 to 21 carbon atoms, thereby adding a fluoroalkyl group and an iodine atom to the 3- and 4-positions of the starting material (there is no regularity upon binding the fluoroalkyl group, that is, the fluoroalkyl group is bound to one of the 3- and 4-positions, and the iodine atom is bound to the position to which the fluoroalkyl group is not bound) (addition reaction step);

(2) replacing the iodine atom in the resulting compound in step (1) with a hydrogen atom (reduction step); and (3) converting the hydroxyl group at the 8- or 9-position of the resulting compound in step (2) to a group $CH_2=CX^2COO-$ (wherein $X^2$ is the same as defined above) (esterification step).

The compound obtained in step (1) (a first intermediate) and the compound obtained in step (2) (a second intermediate) are also included within the scope of the present invention as intermediates for producing the end compound of the present invention and other various compounds.

The first intermediate is a compound represented by formula (I) wherein $R^1$ represents a hydroxy group or a hydrogen atom; $R^2$ represents a hydrogen atom when $R^1$ represents a hydroxy group, or $R^2$ represents a hydroxy group when $R^1$ represents a hydrogen atom; $R^3$ represents a fluoroalkyl group containing from 1 to 21 carbon atoms or an iodine atom; and $R^4$ represents an iodine atom when $R^3$ represents a fluoroalkyl group containing from 1 to 21 carbon atoms, or $R^4$ represents a fluoroalkyl group containing from 1 to 21 carbon atoms when $R^3$ represents an iodine atom.

The second intermediate is a compound represented by formula (I) wherein $R^1$ represents a hydroxy group or a hydrogen atom; $R^2$ represents a hydrogen atom when $R^1$ represents a hydroxy group, or $R^2$ represents a hydroxy group when $R^1$ represents a hydrogen atom; $R^3$ represents a fluoroalkyl group containing from 1 to 21 carbon atoms or a hydrogen atom; and $R^4$ represents a hydrogen atom when $R^3$ represents a fluoroalkyl group containing from 1 to 21 carbon atoms, or $R^4$ represents a fluoroalkyl group containing from 1 to 21 carbon atoms when $R^3$ represents a hydrogen atom.

The end compound of the present invention is a compound represented by formula (I) wherein $R^1$ represents a group $CH_2=CX^2COO-$ or a hydrogen atom; $R^2$ represents a group $CH_2=CX^2COO-$ when $R^1$ represents a hydrogen atom, or $R^2$ represents a hydrogen atom when $R^1$ represents a group $CH_2=CX^2COO-$; $R^3$ represents a fluoroalkyl group containing from 1 to 21 carbon atoms or a hydrogen atom; and $R^4$ represents a hydrogen atom when $R^3$ represents a fluoroalkyl group containing from 1 to 21 carbon atoms, or $R^4$ represents a fluoroalkyl group containing from 1 to 21 carbon atoms when $R^3$ represents a hydrogen atom.

Because the first intermediate contains an iodine atom, it can be utilized to derive other compounds. For example, a carbon-carbon double bond can be formed by reacting the first intermediate with zinc powder in the presence of a solvent (e.g., methyl ethyl ketone, diethyl ether, etc.) at a refluxing temperature to eliminate hydrogen iodide. The resulting compound containing a double bond can be polymerized and the polymer can be shaped to a molded article.

The second intermediate can also be utilized to derive other compounds. For example, the second intermediate can be converted to a glycidyl ether by: dissolving the second intermediate in a solvent such as methyl ethyl ketone or diethyl ether; adding dropwise thereto epichlorohydrin in the presence of a catalyst of boron trifluoride ethyl etherate at room temperature; adding thereto a solid or concentrated aqueous solution of sodium hydroxide; and heating to a temperature of from 80° to 120° C. The resulting glycidyl ether of the second intermediate may be formulated, for example, to an adhesive agent by mixing with a boron trifluoride amine complex.

In the reaction involved in step (1), the molar ratio of the fluoroalkyl iodide to the starting material is usually controlled to be within the range of from 1/0.1 to 1/10, preferably from 1/1.0 to 1/2.0.

In this reaction, a radical initiator may be used. The radical initiator is generally used in an amount of from 0.01 to 30 parts by weight, preferably from 0.5 to 10 parts by weight, per 100 parts by weight of the total weight of the fluoroalkyl iodide and the starting material.

Examples of the radical initiator include: azo compounds such as 2,2'-azobisisobutyronitrile, 2,2'-azobis(2,4-dimethylvalero-nitrile), (1-phenylethyl)azodiphenylmethane, 2,2'-azobis-(4-methoxy-2,4-dimethylvaleronitrile), dimethyl-2,2'-azobisisobutylrate, 2,2'-azobis(2-methylbutyronitrile), 1,1-azobis(1-cyclohexanecarbonitrile), 2-(carbamoylazo)-isobutyronitrile, 2,2'-azobis(2,4,4-trimethylpentane), 2-phenylazo-2,4-dimethyl-4-methoxyvaleronitrile, 2,2'-azobis(2-methylpropane), etc.; diacyl peroxides such as benzoyl peroxide, p-chlorobenzoyl peroxide, etc.; ketone peroxides such as methyl ethyl ketone peroxide, cyclohexanone peroxide, etc.; peresters such as tert-butyl perbenzoate, tert-butylperoxy-2-ethylhexoate, etc.; hydroperoxides such as tert-butyl hydroperoxide, cumene hydroperoxide, etc.; dialkyl peroxides such as di-tert-butyl peroxide, di-sec-butyl peroxide, dicumyl peroxide, etc.; and diaryl peroxides.

The reaction temperature for step (1) is generally in the range of from 0° to 250° C., provided that in the case of using a radical initiator, a temperature which provides a half-lives of 10 minutes or more, or which does not exceed the kick-off temperature of the initiator (at which the initiator begin to decompose abruptly) are preferred.

In addition to the radical initiator, carbonyl compounds of transition metals such as $Ru(CO)_{12}$, $Fe(CO)_{12}$, and $CO_2(CO)_8$, or other metallic catalysts such as copper, ruthenium, and platinum may be employed.

The reaction for step (1) can also be performed under irradiation with visible or ultraviolet rays.

The reduction reaction in step (2) is generally performed by reacting the compound obtained in step (1) with zinc in the presence of a hydrogen halide. Examples of the hydrogen halide include hydrogen chloride, hydrogen bromide, hydrogen iodide, etc. These hydrogen halides are usually employed in the form of solutions in water or ethanol. The reaction may be performed either by adding the hydrogen halide to the mixture of the compound obtained in step (1) and zinc or by adding zinc to the mixture of the compound obtained in step (1) and the hydrogen halide.

The ratio of zinc and the compound obtained in step (1) is from 0.5 to 20 gram atoms of zinc per mole of the compound obtained in step (1). The ratio of zinc and the hydrogen halide is from 1 to 20 gram atoms of zinc per mole of the compound obtained in step (1).

The reduction reaction in step (2) is generally performed using a solvent. Examples of the solvent include those capable of dissolving the compound obtained in step (1) such as alcohols (e.g., methanol, ethanol, n-propanol, and iso-propanol), ketones (e.g., acetone, methyl ethyl ketone, and methyl isobutyl ketone), and ethers (e.g., ethyl ether, propyl ether, and tetrahydrofuran).

The reaction temperature for step (2) is generally in the range of from 0° to 200° C., preferably from 30° to 150° C.

The reaction of esterification in step (3) may be performed by any known method. For instance, the compound obtained in step (2) is reacted with (i) a compound represented by formula: $CH_2=CX^2COOH$ (wherein $X^2$ has the same meaning as defined above), (ii) a compound represented by formula: $CH_2=CX^2COY$ (wherein $X^2$ has the same meaning as defined above; Y represents a fluorine, chlorine, or bromine atom), or (iii) a compound represented by formula: $CH_2=CX^2COOR$ (wherein $X^2$ has the same meaning as defined above; R represents an alkyl group having from 1 to 3 carbon atoms).

Whichever of the reactions (i) to (iii) is carried out, a polymerization inhibitor may be employed to prevent polymerization which might occur as a result of prolonged heating. Examples of the polymerization inhibitor include hydroquinone, hydroquinone monoethyl ether, tert-butyl catechol, catechol, phenothiazine, cupric chloride, etc. These polymerization inhibitors may be used in an amount of from 0.01 to 10 parts by weight per 100 parts by weight of all the reactants employed. The use of the polymerization inhibitor is preferred when the reaction (i) or (iii) is carried out.

The reaction (i) is generally performed by using sulfuric acid, paratoluenesulfonic acid, boron trifluoride ethyl etherate, trifluoromethanesulfonic acid, etc. as a catalyst, and benzene, toluene, xylene, or other organic compounds which undergo azeotropy with water as a solvent. The reaction temperature is generally in the range of from 40° to 200° C.

The reaction (ii) is generally performed by using pyridine, dimethyl aniline, triethylamine, quinoline, metallic magnesium, sodium hydroxide, etc. as an acid acceptor, and with ethyl ether, tetrahydrofuran, acetone, methyl ethyl ketone, chloroform, benzene, etc. as a solvent. The reaction temperature is generally in the range of from 0° to 100° C.

The reaction (iii) is generally performed by using sulfuric acid, paratoluenesulfonic acid, sodium methylate, etc. as a catalyst. In this reaction, because an alcohol represented by formula: ROH (wherein R is the same as defined above) will be generated, the reaction temperature is controlled to be not lower than the boiling of the alcohol in order to remove it. The use of solvents is not necessarily required in this reaction.

The end compound of the present invention as prepared in the steps (1) to (3) described above can be polymerized by any of the known techniques for polymerization of vinyl compounds, e.g., emulsion, bulk, or solution polymerization techniques. The molecular weight of the resulting polymer may be selected depending on the use of the polymer.

In the solution polymerization, the monomers (including the end compound of the present invention) are dissolved in a solvent, a soluble initiator is added, and then the solution is heated at a temperature which gives a convenient decomposition rate of the initiator used until polymerization is essentially completed.

Examples of the solvent which can be used as media in the solution polymerization include benzene, xylene, and toluene.

Preferred initiator-solvent system utilized include those capable of conducting the polymerization reaction at a temperature of from 40° to 100° C., however, systems having broader temperature ranges are also useful.

Examples of the solvent-soluble initiator include an azonitrile such as azobisisobutyronitrile; a peroxyanhydride such as benzoyl peroxide or lauroyl peroxide; a peroxyester such as tert-butyl perbenzoate; and a di-tertalkyl peroxide such as di-tert-butyl peroxide.

The concentration of the monomer in the solution may generally vary from 5 to 95%. The concentration of the initiator is generally in the range of from about 0.01 to about 10% based on the weight of the monomer.

If the solvent itself or other conditions are insufficient to properly control the molecular weight of the resulting polymer, small amounts of chain transfer agents such as alkanethiols having 4 to 12 carbon atoms may be added to the polymerization system.

The resulting polymers can readily be isolated by evaporating the solvent.

The following examples are provided for the purpose of further illustrating the present invention but are in no way to be taken as limiting the scope thereof.

EXAMPLE 1

Addition reaction of fluoroalkyl iodide:

A mixture of 30 g of 8- or 9-hydroxytricyclo[5.2.1.0$^{2,6}$]deca-3-ene, 103 g of a fluoroalkyl iodide represented by formula: n-C$_6$F$_{13}$I, and 0.5 g of azobisisobutyronitrile was charged into a glass reactor equipped with a stirrer, a thermometer, a reflux condenser, and a nitrogen gas blowing pipe. The contents in the reactor were stirred at 85° C. for 14 hours under a nitrogen stream, with 0.5 g of azobisisobutyronitrile being added every 2 hours.

The reaction mixture was distilled under vacuum to obtain fractions of 120° to 126° C./3 mmHg in a yield of 46 g.

The resulting product was a mixture of the following four compounds.

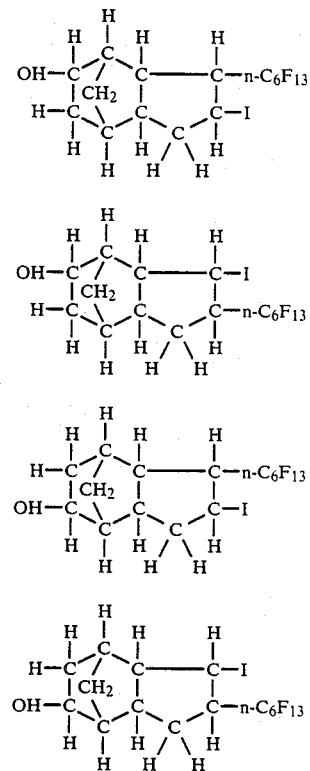

Elemental analysis for C$_{16}$H$_{14}$F$_{13}$IO:
Calculated: 32.33% C, 2.37% H, 41.43% F.
Found: 31.67% C, 2,40% H, 41.01% F.

NMR spectroscopy: $^1$H-NMR (solvent, CDCl$_3$; internal reference, TMS; the same applies to all examples that follow);

δ(ppm)=1.2–2.8 (12H), 4.7 (1H, —CHI—).

$^{19}$F-NMR (solvent, CDCl$_3$; external reference, CF$_3$COOH; the higher magnetic field on the positive side; the same applies to all examples that follow);

δ(ppm)=2.4 (3F, m, CF$_3$—), 37.9, 42.6, 43.2, 44.1, 47.5 (10F, (CF$_2$)$_5$)

EXAMPLE 2

Addition reaction of fluoroalkyl iodide:

A reaction was carried out by the same procedures as in Example 1 except that 126 g of a fluoroalkyl iodide represented by formula: n-$C_8F_{17}$I was substituted for the fluoroalkyl iodide used in Example 1. Fractions of 132° to 137° C./2 mmHg were obtained in a yield of 38 g.

The resulting product was a mixture of the following four compounds.

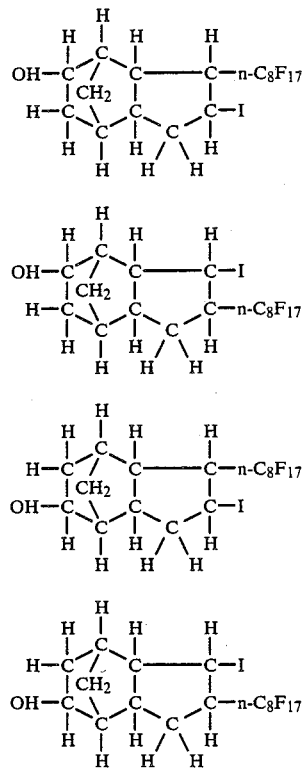

Elemental analysis for $C_{18}H_{14}F_{17}IO$: Calculated: 31.05% C, 2.03% H, 49.4% F. Found: 31.68% C, 1.98% H, 48.91% F.

NMR spectroscopy: $^1$H-NMR; δ(ppm)=1.2-2.8 (12H), 4.7 (1H, —CHI—).

EXAMPLE 3

Addition reaction of fluoroalkyl iodide:

The same compounds were charged in the same proportions as in Example 1 except that azobisisobutyronitrile was replaced by the same amount of benzoyl peroxide. The reaction was performed at 85° C. for 20 hours, with 0.5 g of benzoyl peroxide being added every 5 hours. Fractions of 120° to 126° C./3 mmHg were obtained in a yield of 32 g.

The resulting product was a mixture of the following four compounds.

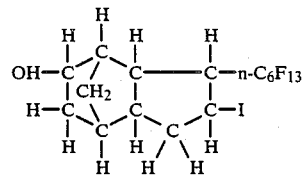
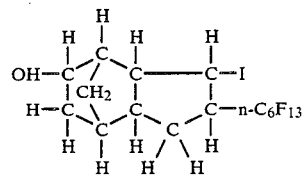
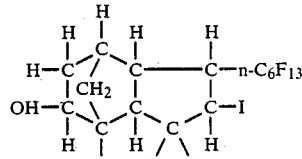
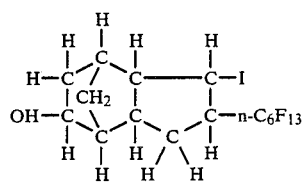

Elemental analysis for $C_{16}H_{14}F_{13}IO$: Calculated: 32.33% C, 2.37% H, 41.43% F. Found: 31.86% C, 2.39% H, 40.97% F.

NMR spectroscopy: 1H-NMR; δ(ppm)=1.2-2.8 (12H), 4.7 (1H, —CHI—)

EXAMPLE 4

Addition reaction of fluoroalkyl iodide:

30 g of 8- or 9-hydroxy-tricyclo[5.2.1.0$^{2,6}$]deca-3-ene and 80 g of a fluoroalkyl iodide represented by formula: n-$C_4F_9$I were charged into a Pyrex reactor and subjected to reaction under illumination with a high-pressure mercury lamp for 10 days at 25° C. Fractions of 102° to 105° C./3 mmHg were obtained in a yield of 47 g.

The resulting product was a mixture of the following four compounds.

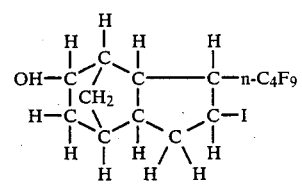
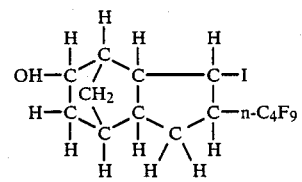
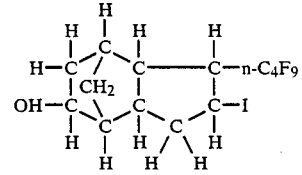

Elemental analysis for $C_{14}H_{14}F_9IO$: Calculated: 33.89% C, 2.84% H, 34.74% F. Found: 33.01% C, 2.72% H, 33.93% F.

NMR spectrocopy: $^1H$-NMR; $\delta(ppm)=1.2-2.8$ (12H), 4.7 (1H, —CHI—)

EXAMPLE 5

Reduction reaction:

A reactor equipped with a stirrer and a reflux condenser was charged with a slurry made of 6.5 g (0.1 gram atom) of a zinc powder and 25 ml of 99.5% ethanol and a solution made up of 24 g (0.04 moles) of the compound obtained in Example 1 and 50 ml of 99.5% ethanol. To the mixture, 1.2 ml of 55% hydroiodic acid was added. The mixture was refluxed by heating for 5 minutes, followed by addition of 2.5 ml of 55% hydroiodic acid. After one hour, a slurry made of 6.5 g of a zinc powder and 25 ml of 99.5% ethanol and 1.2 ml of 55% hydroiodic acid were successively added and the mixture was refluxed by heating for 1 hour. The reaction mixture was cooled and then filtered. The filtrate was poured into 1,000 ml of water and extracted twice with 400 ml of ethyl ether. The ether layer was dried with a mixture of anhydrous sodium carbonate and anhydrous sodium sulfate, and concentrated. The concentrate was distilled under vacuum to obtain fractions of 117° to 120° C./4 mmHg in a yield of 15 g.

The resulting product was a mixture of the following four compounds.

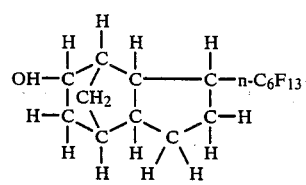

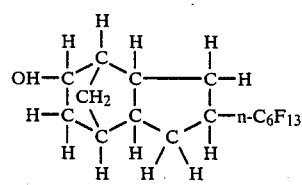

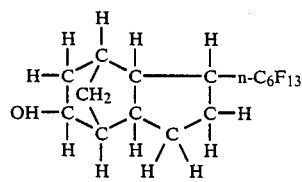

Elemental analysis for $C_{16}H_{15}F_{13}O$: Calculated: 40.86% C, 3.22% H, 52.52% F. Found: 40.29% C, 3.33% H, 51.96% F.

NMR spectroscopy: $^1H$-NMR; $\delta(ppm)=1.0-2.9$ (14H), 3.8

(1H, HO—C$\underline{H}$—), $^{19}F$-NMR; $\delta(ppm)=2.5$ (3F, m, CF$_3$—), 38.0, 42.7, 43.3, 44.3, 47.6 (10F, (CF$_2$)$_5$)

EXAMPLE 6

Reduction reaction:

A reaction was performed in the same manner as in Example 5 except that the compound prepared in Example 1 was replaced by 28 g of the compound prepared in Example 2. Fractions of 126° to 130° C./4 mmHg were obtained in a yield of 16 g.

The resulting product was a mixture of the following four compounds.

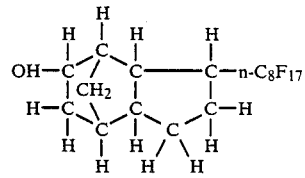

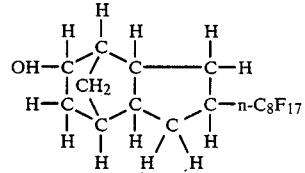

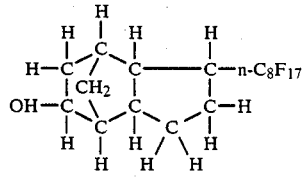

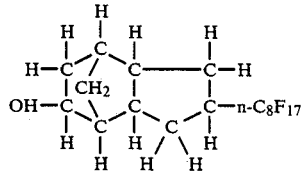

Elemental analysis for $C_{18}H_{15}F_{17}O$: Calculated: 37.91% C, 2.65% H, 56.64% F. Found: 38.20% C, 2.60% H, 56.03% F.

NMR spectroscopy: $^1H$-NMR; $\delta(ppm)=1.0-2.9$ (14H), 3.8 (1H, HO—CH—)

EXAMPLE 7

Reduction reaction:

Into a solution made up of 74.4 g (0.15moles) of the compound prepared in Example 4 and 100 ml of absolute ethanol, dry hydrogen chloride as was bubbled so as to saturated. To the saturated solution, a slurry made of 10 g of a zinc powder and 50 ml of absolute ethanol was slowly added with stirring, whereupon foaming and heat generation occurred. Thereafter, the mixture was stirred at 70° C. for 1 hour. The same amount of a slurred zinc powder as above was further added to the mixture which was saturated with a dry bubbled gas of hydrogen chloride, followed by stirring at 70° C. for 1 hour. The mixture was cooled to room temperature and then filtered. The filtrate was poured into a large amount of ice water, and then extracted with ethyl ether and dried with a mixture of anhydrous sodium carbonate and anhydrous sodium sulfate. After distilling off ethyl ether, the dried solution was distilled under vacuum to obtain fractions of 88° to 91° C./4 mmHg in a yield of 33 g.

The resulting product was a mixture of the following four compounds.

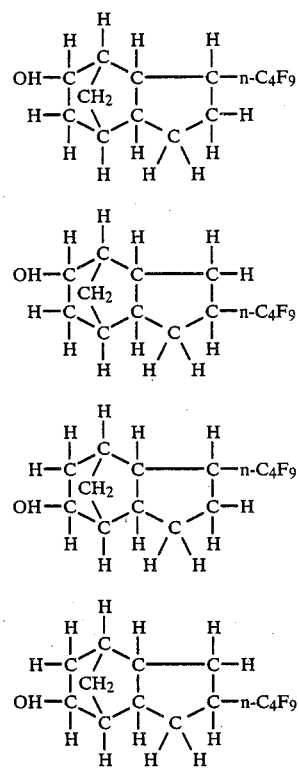

Elemental analysis for $C_{14}H_{15}F_9O$: Calculated: 45.41% C, 4.08% H, 46.18% F. Found: 45.00% C, 3.91% H, 46.68% F.

EXAMPLE 8

Esterification reaction:

15 g of triethylamine was added to a solution made up of 47 g of the compound prepared in Example 5 and 70 ml of ethyl ether. To the mixture, 16 g of methacryloyl chloride was added dropwise over 10 minutes. The resulting reaction solution was stirred for 4 hours with cooling conducted to maintain at a temperature of 20° C. or less. The reaction mixture was poured into 1,000 ml of water and extracted with 200 ml of benzene. The benezene layer was washed with 2% aqueous sodium hydroxide and further washed with saturated aqueous sodium chloride until the aqueous layer would no longer show alkaline condition. The benzene layer was dried with anhydrous magnesium sulfate and then filtered. Thereafter, benzene and ether were distilled off under vacuum at 50° C. or less. An esterified product was obtained in a yield of 36 g.

The resulting product was a mixture of the following four compounds.

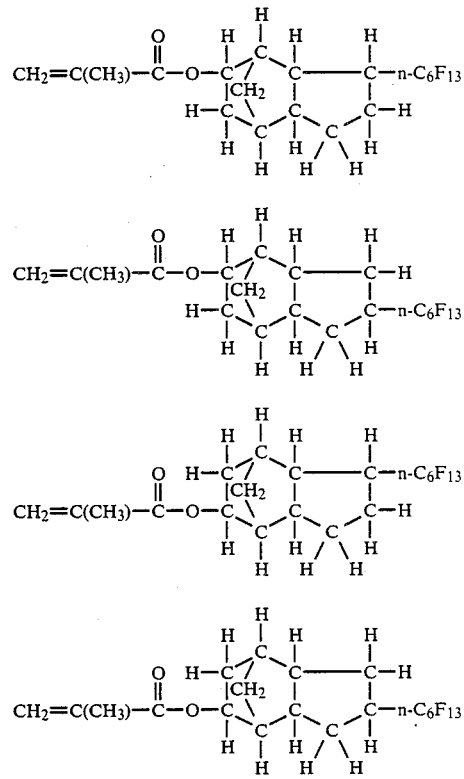

Elemental analysis for $C_{20}H_{19}F_{13}O_2$: Calculated: 44.62% C, 3.56% H, 45.88% F. Found: 44.12% C, 3.56% H, 45.21% F.

NMR spectroscopy: $^1$H-NMR;

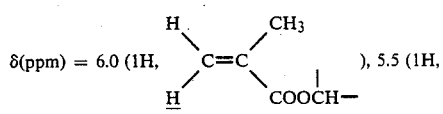

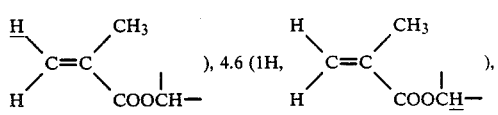

1.1–2.9 (16H)

EXAMPLE 9

Esterification:

An esterified product was prepared in a yield of 31 g by repeating the procedures of Example 8 except that methacryloyl chloride was replaced by 14 g of acryloyl chloride.

The resulting product was a mixture of the following four compounds:

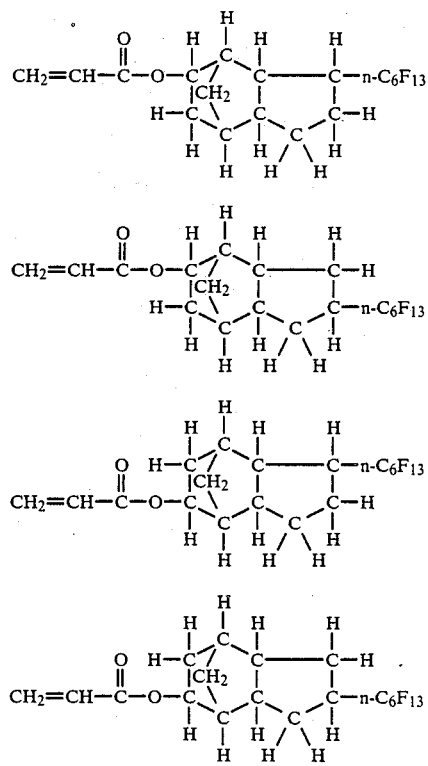

Elemental analysis for $C_{19}H_{17}F_{13}O_2$: Calculated: 43.42% C, 3.27% H, 47.11% F. Found: 43.81% C, 3.06% H, 46.66% F.

NMR spectrocopy: $^1$H-NMR;

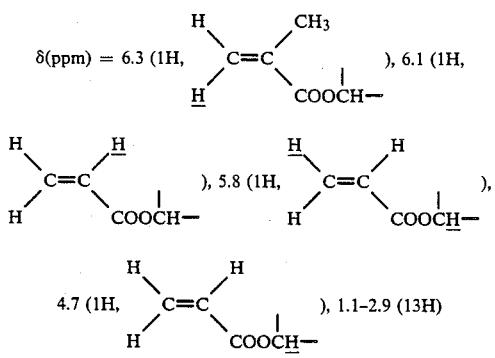

EXAMPLE 10

Esterification reaction:

24 g of α-trifuoromethylacryloyl chloride was added to a solution made of 47 g of the compound prepared in Example 5 and 70 ml of ethyl ether, and the mixture was cooled to 10° C. or less. To the mixture stirred, a solution made of 6 g of sodium hydroxide and 40 ml of water was added dropwise in small portions so that the temperature of the reaction solution was held at 10° C. or less. After completion of the addition, the cooling was stopped and the mixture was stirred for an additional 4 hours. The reaction mixture was poured into 1,000 ml of water and the resulting solution was extracted with 200 ml of benzene. The benzene layer was washed with 2% aqueous sodium hydroxide and subjected to repeated washing with saturated aqueous sodium chloride until the aqueous layer would no longer show alkaline consition. The benzene layer was dried with anhydrous magnesium sulfate and then filtered. Benzene and ether were distilled off under vacuum at 50° C. and below to obtain a pale yellow oilly product (end compound) in a yield of 32 g.

The resulting product was a mixture of the following four compounds.

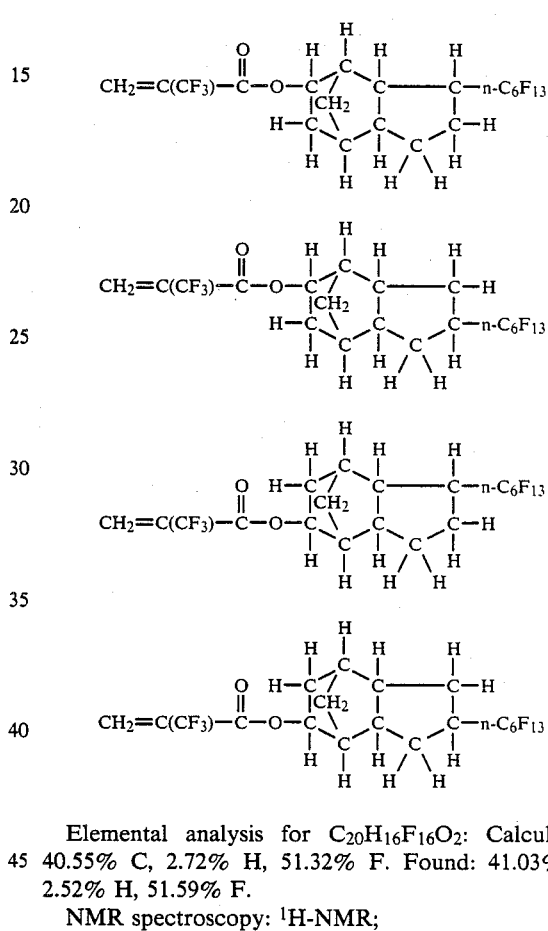

Elemental analysis for $C_{20}H_{16}F_{16}O_2$: Calculated: 40.55% C, 2.72% H, 51.32% F. Found: 41.03% C, 2.52% H, 51.59% F.

NMR spectroscopy: $^1$H-NMR;

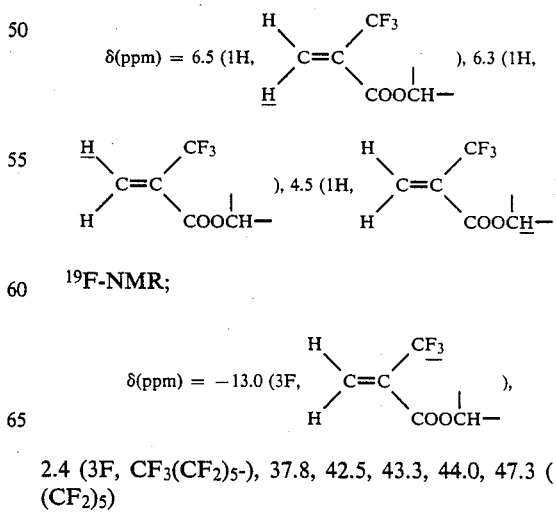

2.4 (3F, $CF_3(CF_2)_5$-), 37.8, 42.5, 43.3, 44.0, 47.3 (10F, $(CF_2)_5$)

EXAMPLE 11

Esterification reaction:

Esterification was performed in the same manner as in Example 10 except that the compound prepared in Example 5 was replaced by 57 g of the compound prepared in Example 6.

The resulting product was a mixture of the following four compounds.

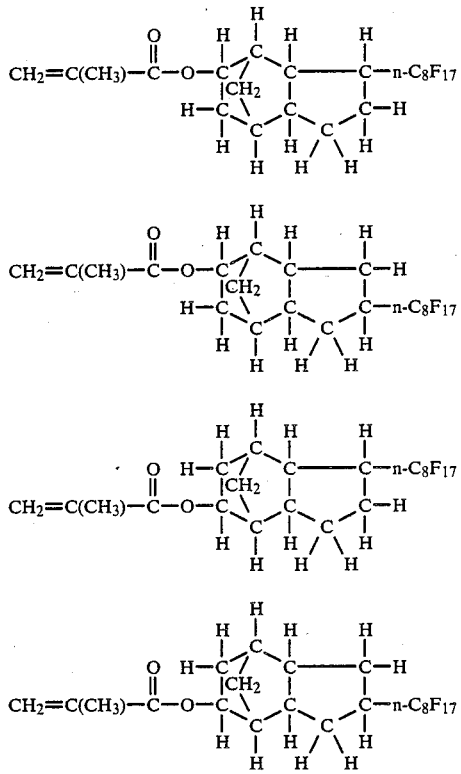

Elemental analysis for $C_{22}H_{19}F_{17}O_2$: Calculated: 41.39% C, 3.00% H, 50.60% F. Found: 41.61% C, 3.08% H, 49.98% F.

EXAMPLE 12

Esterification reaction:

A mixture of 74 g of the compound prepared in Example 7, 26 g of methacrylic acid, 150 ml of toluene, 2 g of sulfuric acid, and 0.5 g of hydroquinone monomethyl ether was charged into a glass reactor equipped with a stirrer, a water separator, a reflux condenser, and a thermometer. The contents were heated under reflux. Water which flowed out from the reactor as an azeotrope with toluene was separated with water separator and the toluene was continuously returned to the reactor. After heating for 8 hours, the reaction mixture was cooled to room temperature. A total of about 3 ml of water had flowed out from the reactor. To the reaction mixture, 100 ml of benzene was added and the resulting mixture was washed first with a saturated aqueous solution of sodium carbonate, then with a saturated aqueous solution of sodium chloride until the aqueous layer would no longer show alkaline condition. The benzene layer was dried with anhydrous magnesium sulfate and the solvent was removed by distillation under vacuum. To the residue, 2 g of cupric chloride was added and the mixture was distilled off under vacuum to obtain feractions of 101° to 104° C./2 mmHg in a yield of 29 g.

The resulting product was a mixture of the following four compounds.

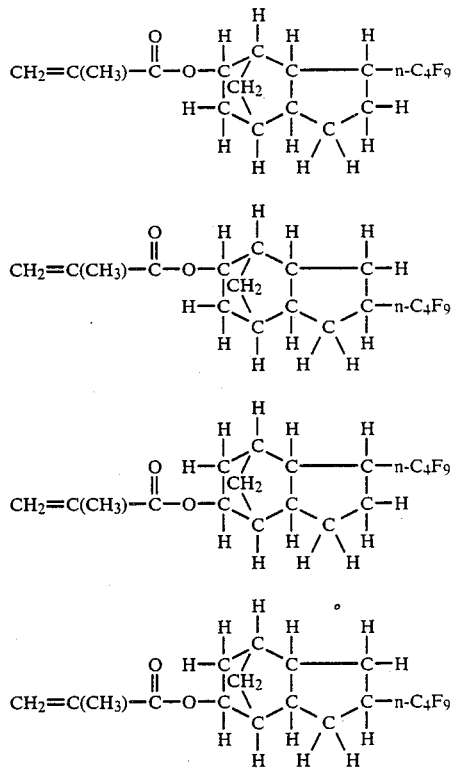

Elemental analysis for $C_{18}H_{19}F_9O_2$: Calculated: 49.32% C, 4.37% H, 39.01% F. Found: 49.33% C, 4.42% H, 38.66% F.

TEST EXAMPLE 1

95 parts by weight of the acrylate prepared in Example 9 was mixed with 5 parts by weight of 2-hydroxyethyl acrylate and 5 parts by weight of benzoin ethyl ether. The mixture was applied onto a glass plate with a bar coater to form a coating about 20 μm thick which was illuminated for 1 minute under a high-pressure mercury lamp (100 W/cm) placed 10 cm above the glass plate. The glass plate was submerged in boiling water for 2 hours but no change occurred in the coating, which was therefore found to have cured completely and adhered strongly to the glass plate.

A comparative coating was formed and cured by repeating the same procedures as described above except that a commercial product of tricyclodecanyl acrylate (FA-513A produced by Hitachi Chemical Co., Ltd.) was substituted for the acrylate prepared in Example 9. After immersion in boiling water for 2 hours, blushing and blistering occurred in some portions of the coating.

EXAMPLE 13

500 parts by weight of the product obtained in Example 8, 50 parts by weight of toluene, and 0.2 parts by weight of azobisisobutyronitrile were placed in a glass ampule and sealed under a nitrogen atomosphere. The ampule was allowed to stand for 36 hours in a thermostat at a temperature of 60° C. Thereafter, the content of the ampule was collected, and toluene was removed by evaporating at 35 mmHg and 100° C. to obtain a polymer.

The polymer had a glass transition point of 102° C. and a heat decomposition temperature of 240° C. (in the atmosphere; temperature rising rate of 10° C./min; at a weight decrease of 5 wt %).

TEST EXAMPLE 2

A comparative polymer was prepared in the same manner as in Example 13 except that 3,4-dibromotricyclo-[5.2.1.0$^{2,6}$]decyl methacrylate was used instead of the product of Example 8.

The polymer obtained in Example 13 and the above comparative polymer each was molded by a hot press to a disc having a thickness of 3 mm and a diameter of 50 mm, and immersed in boiling water at 100° C. for 2 hours so as to determine the hygroscopicity by measuring the increase in weight.

The hygroscopicity of the polymer of Example 13 was 0.02% and that of the comparative polymer was 0.24%.

A polymer containing the tricyclodecane derivative of the present invention as a monomeric component exhibits a higher resistance to water and fouling but a lower degree of hygroscopicity than conventional analogues. Therefore, this polymer is useful as a painting or optical material.

While the invention has been described in detail and with reference to specific examples thereof, it will be apparent to one skilled in the art that various changes and modifications can be made therein without departing from the spirit and scope thereof.

What is claimed is:

1. A tricyclodecane derivative represented by formula (I):

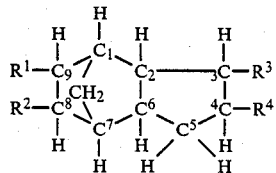

wherein
$R^1$ represents a group $X^1O$— or a hydrogen atom;
$R^2$ represents a hydrogen atom when $R^1$ represents a group $X^1O$—, or $R^2$ represents a group $X^1O$— when $R^1$ represents a hydrogen atom;
wherein $X^1$ represents a group

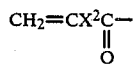

or a hydrogen atom, wherein $X^2$ represents a hydrogen atom, a methyl group, or a trifluoromethyl group;
$R^3$ represents a fluoroalkyl group containing from 1 to 21 carbon atoms, an iodine atom, or a hydrogen atom; and
$R^4$ represents an iodine atom or a hydrogen atom when $R^3$ represents a fluoroalkyl group containing from 1 to 21 carbon atoms, or $R^4$ represents a fluoroalkyl group containing from 1 to 21 carbon atoms when $R^3$ represents an iodine atom or a hydrogen atom.

2. A tricyclodecane derivative as claimed in claim 1, wherein
$R^1$ represents a hydroxy group or a hydrogen atom;
$R^2$ represents a hydrogen atom when $R^1$ represents a hydroxy group, or $R^2$ represents a hydroxy group when $R^1$ represents a hydrogen atom;
$R^3$ represents a fluoroalkyl group containing from 1 to 21 carbon atoms or an iodine atom; and
$R^4$ represents an iodine atom when $R^3$ represents a fluoroalkyl group containing from 1 to 21 carbon atoms, or $R^4$ represents a fluoroalkyl group containing from 1 to 21 carbon atoms when $R^3$ represents an iodine atom.

3. A tricyclodecane derivative as claimed in claim 1, wherein
$R^1$ represents a hydroxy group or a hydrogen atom;
$R^2$ represents a hydrogen atom when $R^1$ represents a hydroxy group, or $R^2$ represents a hydroxy group when $R^1$ represents a hydrogen atom;
$R^3$ represents a fluoroalkyl group containing from 1 to 21 carbon atoms or a hydrogen atom; and
$R^4$ represents a hydrogen atom when $R^3$ represents a fluoroalkyl group containing from 1 to 21 carbon atoms, or $R^4$ represents a fluoroalkyl group containing from 1 to 21 carbon atoms when $R^3$ represents a hydrogen atom.

4. A tricyclodecane derivative as claimed in claim 1, wherein
$R^1$ represents a group

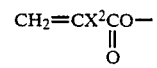

or a hydrogen atom;
$R^2$ represents a group

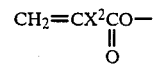

when $R^1$ represents a hydrogen atom, or $R^2$ represents a hydrogen atom when $R^1$ represents a group

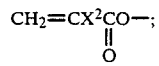

$R^3$ represents a fluoroalkyl group containing from 1 to 21 carbon atoms or a hydrogen atom; and
$R^4$ represents a hydrogen atom when $R^3$ represents a fluoroalkyl group containing from 1 to 21 carbon atoms, or $R^4$ represents a fluoroalkyl group containing from 1 to 21 carbon atoms when $R^3$ represents a hydrogen atom.

5. A tricyclodecane derivative as claimed in claim 1, wherein said fluoroalkyl group represented by $R^3$ or $R^4$ contains fluorine atoms in an amount of the same number or more as the number of the carbon atoms contained in said group.

6. A tricyclodecane derivative as claimed in claim 5, wherein said fluoroalkyl group represented by $R^3$ or $R^4$ contains fluorine atoms in an amount of 2 times or more the number of the carbon atoms contained in said group.

7. A tricyclodecane derivative as claimed in claim 6, wherein said fluoroalkyl group represented by $R^3$ or $R^4$ is a perfluoroalkyl group.

8. A tricyclodecane derivative as claimed in claim 1, wherein said fluoroalkyl group represented by $R^3$ or $R^4$ contains from 2 to 10 carbon atoms.

9. A polymer comprising monomeric units derived from said tricyclodecane derivative as claimed in claim 4.

* * * * *